United States Patent
Karim et al.

(10) Patent No.: US 6,441,227 B1
(45) Date of Patent: Aug. 27, 2002

(54) TWO STAGE PROCESS FOR THE PRODUCTION OF UNSATURATED CARBOXYLIC ACIDS BY OXIDATION OF LOWER UNSATURATED HYDROCARBONS

(75) Inventors: Khalid Karim, Manchester (GB); Yajnavalkya Subrai Bhat, Riyadh (SA); Asad Ahmad Khan, Riyadh (SA); Syed Irshad Zaheer, Riyadh (SA); Abdullah Bin Nafisa, Riyadh (SA)

(73) Assignee: Saudi Basic Industries Corporation (SA)

( * ) Notice: Subject to any disclaimer, the term of this patent is extended or adjusted under 35 U.S.C. 154(b) by 0 days.

(21) Appl. No.: 09/602,784

(22) Filed: Jun. 23, 2000

(51) Int. Cl.$^7$ ............................................. C07C 51/25
(52) U.S. Cl. ...................... 562/548; 562/546; 562/547; 562/607
(58) Field of Search ................................ 562/546, 547, 562/548, 607

(56) References Cited

U.S. PATENT DOCUMENTS

| | | | |
|---|---|---|---|
| 4,321,160 A | * 3/1982 | Farrington et al. | 252/437 |
| 4,365,087 A | 12/1982 | Kadowaki et al. | |
| 5,071,814 A | * 12/1991 | Sasaki et al. | 502/205 |
| 5,077,434 A | 12/1991 | Baromaru et al. | |
| 5,218,146 A | * 6/1993 | Takata et al. | 562/535 |
| 5,602,280 A | 2/1997 | Nagai et al. | |

FOREIGN PATENT DOCUMENTS

| | | |
|---|---|---|
| DE | 3002829 | 7/1980 |
| EP | 145469 | 6/1985 |
| EP | 293224 | 11/1988 |
| EP | 630879 | 12/1994 |
| EP | 911313 | 4/1999 |
| JP | 59013746 | 1/1984 |
| JP | 1165543 | 6/1989 |

* cited by examiner

Primary Examiner—Johann Richter
Assistant Examiner—Robert W. Deemie
(74) Attorney, Agent, or Firm—Kramer Levin Naftalis & Frankel

(57) ABSTRACT

A process for the production of alpha-beta unsaturated carboxylic acid with high yield at low temperature and atmospheric pressure, includes two stages for catalytic vapor-phase oxidation of olefins with molecular oxygen. In a first stage, olefins are oxidized using catalyst A having a composition according to the formula $$Mo_a Pd_b Bi_c Fe_d X^1_e X^2_f X^3_g O_z,$$

wherein
$X^1$=one or more of Co, Ni, V, Pt, Rh; $X^2$=one or more of Al, Ga, Ge, Mn, Nb, Zn, Ag, P, Si, W; $X^3$=at least one or more of K, Mg, Rb, Ca, Sr, Ba, Na; and O=oxygen; to produce a first stage product containing alpha-beta unsaturated aldehydes In a second stage, alpha-beta unsaturated aldehydes in the first stage product are oxidized using catalyst B having a composition according to the formula $$Mo_{a_1} V_{b_1} Al_{c_1} X_{d_1} Y_{e_1} O_{z_1}$$

wherein
X=W or Mn or both; Y=at least one or more of Pd, Sb, Ca, P, Ga, Ge, Si, Mg, Nb, K; and O is oxygen which satisfies the valences of the other elements; to produce mainly alpha-beta unsaturated carboxylic acid. A portion of the oxygen is introduced into the reaction stream between the first and second stages or in multistages. More particularly, the invention relates to a two stage process for catalytic oxidation of propylene or isobutylene to yield acrylic acid or methacrylic acid.

16 Claims, 1 Drawing Sheet

TWO STAGE PROCESS FOR THE PRODUCTION OF UNSATURATED CARBOXYLIC ACIDS BY OXIDATION OF LOWER UNSATURATED HYDROCARBONS

BACKGROUND OF THE INVENTION

1. Field of the Invention

This invention relates to a two-stage process for the production of alpha-beta carboxylic acids through catalytic vapor-phase oxidation of olefins by molecular oxygen using mixed metal oxide catalysts having the formulas A) $Mo_aPd_bBi_cFe_dX^1_eX^2_fX^3_gO_z$ ($X^1$=Co, Ni, V, Pt and/or Rh; $X^2$=Al, Ga, Ge, Mn, Nb, Zn, Ag, P and/or Si; $X^3$=K, Mg, Rb, Ca, Sr, Ba and/or Na); and B) $Mo_{a_1}V_{b_1}Al_{c_1}X_{d_1}Y_{e_1}O_{z_1}$ (X=W or Mn or both; Y=Pd, Sb, Ca, P, Ga, Ge, Si, Mg, Nb and/or K). The exothermic nature (exothermicity) or ΔT of the oxidation reaction can be controlled by addition of oxygen at an intermediate stage of the process while achieving same high output yield and catalyst life of the overall reaction.

2. Description of the Related Art

A two stage vapor phase oxidation process for the production of acrylic acid from propylene is well known in the art. Attempts have been made to improve the productivity of a process for production of acrylic acid by using different types of catalysts and process parameters, described, e.g., in JP1165543; JP59013746; EP911313; U.S. Pat. No. 5,602, 280 (EP0630879); EP145469; U.S. Pat. No. 5,218,146 (EP293224); U.S. Pat. No. 4,365,087 (DE3002829); and U.S. Pat. No. 5,077,434. For example, U.S. Pat. No. 5,218, 146 describes a process for the production of acrylic acid by a two-stage catalytic vapor-phase oxidation of propylene with molecular oxygen: the first stage oxidizes propylene to produce mainly acrolein and the second stage oxidizes acrolein to produce mainly acrylic acid. In this process there is supplied to the first stage reaction, a raw gas containing a saturated aliphatic hydrocarbon having 1 to 5 carbon atoms in an amount in the range of 5–70% by volume, carbon dioxide in an amount in the range 3–50% by volume, aliphatic hydrocarbon and carbon dioxides in a total amount in the range of 20 to 80% by volume and the gas also contains steam in an amount in the range of 0.5 to 8 mol per mol of propylene.

Further process improvements are needed to deal with problems in the removal of heat of the reaction, in space velocity, in limitations on the life of the catalyst due to ineffective heat removal and in limitations in catalyst activity related to its composition.

It is an object of the present invention to provide a substantially safe process for the production of acrylic acid by the catalytic vapor phase oxidation of propylene with a high productivity.

It is a further object of the invention to provide a process for the production of an acrylic acid or methacrylic acid from propylene or isobutylene in which ΔT of reaction is lower because of the specific composition of catalysts. A lower ΔT enhances the life of the catalyst.

It is another object of the invention to provide a process which exhibits long-term operation or stability in term of catalyst performance by intermediate addition of oxygen in between the two stages of the process, or at multistages in the process.

SUMMARY OF THE INVENTION

The invention relates to a process for the production of carboxylic acids using a two-stage catalytic vapor-phase oxidation of olefins. The invention also includes a new catalyst for the first stage of the process.

The process comprises:

introducing into a first stage reactor, a feedstream comprising olefins, oxygen, steam and inert gas, subjecting the feedstream to oxidizing conditions in the first stage to produce an intermediate product stream comprising aldehydes;

introducing the intermediate product stream into a second stage reactor under aldehyde oxidizing conditions to produce a second stage product comprising carboxylic acid.

Besides introduction of oxygen into the first stage, oxygen can also be introduced into the product stream intermediate between the first and second stages or at multistages within the same reaction zone or reactor.

Moreover, the second stage product is a mixed reaction gas which contains off-gas and carboxylic acid product. Off-gas obtained by separating carboxylic acid from the second stage mixed reaction gas product can be recycled to the first stage. In addition, steam can also be present in the second stage mixed reaction gas product. Steam obtained by separating the carboxylic acid product from the mixed reaction gas product can be supplied to the first stage.

The olefins are, for example, ethylene, propylene, or iso- or n-butylenes; and the aldehydes are, for example, acetaldehyde, acrolein and methacrolein, producing corresponding carboxylic acids.

In a first stage, olefins are oxidized to produce an intermediate product stream containing alpha-beta unsaturated aldehydes using catalyst A having a composition according to the formula

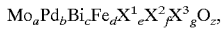

wherein $X^1$=one or more of Co, Ni, V, Pt, Rh;

$X^2$=one or more of Al, Ga, Ge, Mn, Nb, Zn, Ag, P, Si, W;

$X^3$=at least one or more of K, Mg, Rb, Ca, Sr, Ba, Na; and

O=oxygen (which satisfies the valences of the other elements);

and wherein a, b, c, d, e, f, g, and z are as defined below.

In a second stage, alpha-beta unsaturated aldehydes in the intermediate product stream are oxidized to produce mainly alpha-beta unsaturated carboxylic acid using catalyst B having a composition according to the formula

wherein

X=W or Mn or both;

Y=at least one or more of Pd, Sb, Ca, P, Ga, Ge, Si, Mg, Nb, K; and

O is oxygen which satisfies the valences of the other elements;

and wherein $a_1, b_1, c_1, d_1, e_1$ and $z_1$ are as defined below.

In a preferred embodiment, the invention relates to a process for the production of alpha-beta carboxylic acids, such as acrylic acid or methacrylic acid, by the catalytic vapor-phase oxidation of olefins, such as propylene or isobutylene. More particularly, the invention relates to a process for highly efficient production of acrylic acid or methacrylic acid through the use of a feed gas having a particular composition. In the production of acrylic acid by a two-stage catalytic vapor-phase oxidation of propylene with molecular oxygen, a first stage oxidizes propylene to produce mainly acrolein and the second stage oxidizes acrolein to produce mainly acrylic acid.

In preferred embodiments, a gas mixture is supplied to the first stage. The gas mixture preferably contains unsaturated aliphatic hydrocarbon of about C1 to C5, most preferably propylene or isobutylene, in an amount from about 3% to about 90%; oxygen in an amount from about 2% to about 50%; steam in an amount from about 5% to about 50% by volume; and 5% to 80% inert gas or gas with high specific heat such as nitrogen, argon, propane, carbon dioxide.

Additional oxygen in an amount from about 2% to 50% can be added at an intermediate stage of the process or at multiple stages in the reaction zone, in order to control the total oxidation reaction and to achieve a long catalyst life and high productivity of the acrylic acid. The part of the amount of oxygen added at an intermediate stage or multi-stage is preferably from about 2% to about 15% by volume.

A catalytic process according to the present invention shows improvement in the catalyst performance and/or good catalyst stability. While it is not intended to be bound by theory, it is believed that these improvements can be attributed to low ΔT of the reaction and introduction of oxygen at multi- or intermediate stages of the reaction zones to control the extent of exotherm and keep the reaction mixture out of explosive regimes or explosive ranges. Moreover, catalysts provided to carry out the reactions are relatively active at lower temperature than temperatures described in the prior art.

DETAILED DESCRIPTION OF THE INVENTION

Figure 1:
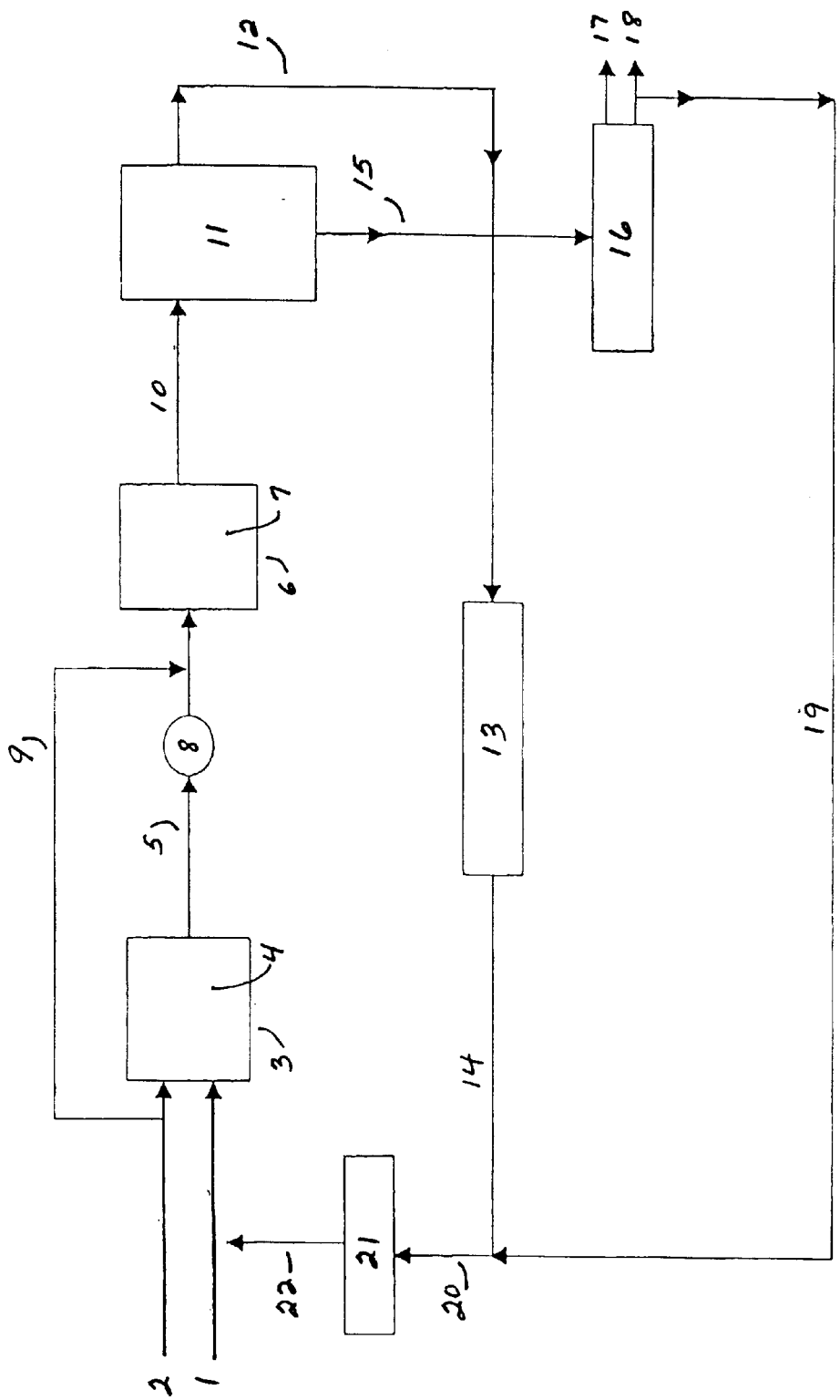
FIG. 1 is a schematic diagram illustrating the process of the invention.

In a preferred reaction gas composition, a content of olefin, e.g., propylene or isobutylene, is in the range of 1% to 50% by volume, preferably 3% to 30% by volume; a content of oxygen (air, molecular oxygen, or mixture thereof) is in the range of 5% to 40% by volume, preferably 8% to 30% by volume; a content of carbon dioxide is in the range of 3% to 50% by volume, preferably 5% to 40% by volume, with a total content of hydrocarbon and carbon dioxide in the range of 20% to 80% by volume, preferably 30% to 70% by volume; and a content of steam is in the range of 3% to 50% by volume, preferably 5% to 40% by volume.

Preferably, the molecular oxygen is supplied as a molecular oxygen-containing gas having purity of at least 95% by volume.

Preferably, recycle gas obtained by separating carboxylic acid, e.g., acrylic acid, from the mixed reaction gas produced by the second-stage reaction can be fed to the first-stage reaction, which can have a large thermal effect as well in controlling the ΔT of the reaction. Conveniently, the steam to be supplied to the first-stage reaction is the steam contained in the recycle gas obtained by separating acrylic acid from the mixed reaction gas produced by the second-stage reaction. Build up gases may be purged.

Preferably the reaction in the first-stage is carried out in the presence of an oxide catalyst A (CAT-A), as more fully described in U.S. patent application Ser. No. 09/560989, and the reaction in the second-stage is carried out in the presence of an oxide catalyst B (CAT-B), as more fully described in U.S. patent application Ser. No. 09/560988.

CAT-A is mixed metal oxide catalyst in a composition having a formula

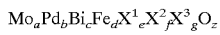

$$Mo_a Pd_b Bi_c Fe_d X^1_e X^2_f X^3_g O_z$$

wherein $X^1$=at least one or more of Co, Ni, V, Pt, Rh $X^2$=at least one or more of Al, Ga, Ge, Mn, Nb, Zn, Ag, P, Si, W $X^3$=at least one or more of K, Mg, Rb, Ca, Sr, Ba, Na, In O=oxygen, and a is 1

$0<b\leq0.3$ $0<c\leq0.9$ $0<d\leq0.9$ $0<e\leq0.9$ $0<f\leq0.9$ $0<g<0.3$.

z is a number which satisfies the valences of the other elements in the formula.

CAT-B is mixed metal oxides in a composition having the formula

$$Mo_{a_1} V_{b_1} Al_{c_1} X_{d_1} Y_{e_1} O_{z_1}$$

wherein

X=W or Mn or both,

Y=at least one or more of Pd, Sb, Ca, P, Ga, Ge, Si, Mg, Nb, K

O is oxygen, and $a_1$ is 1, $b_1$ is 0.01 to 0.9, $0<c_1\leq0.2$, $0<d_1\leq0.5$, $0<e_1\leq0.5$, $z_1$ is a number which satisfies the valences of the other elements in the formula.

Catalysts A and B can used over supports in the form of shapes, or in fluidizable form. Suitable supports for the catalyst include alumina, silica, titania, zirconia, zeolites, silicon carbide, Mo carbide, molecular sieves and other microporous or nonporous materials, and mixtures thereof. Support material can be pretreated with acids such as HCl, $HNO_3$, $H_2SO_4$, peracids or heteropoly acids and alkali base materials. When used on a support, the supported catalyst usually comprises from about 5% to 90% by weight of the catalyst composition, with the remainder being the support material.

Heat of the reaction for oxidation process is related to the concentration of the oxygen or extent of oxidation reaction, which ultimately affects reaction product selectivity. For a two stage oxidation process, addition of oxygen at intermediate level, maintains the yield, while having a positive impact on the amount of heat generated and removed out of the reaction zone. This results in an optimum rate of partial oxygenation or total oxidation, depending on the type of the catalyst. In addition, propane, carbon dioxide and other gases with higher specific heat capacity can also be used to remove heat of the reaction in order to eliminate the possibility of explosion. Steam in an adequate amount as a co-feed is used to promote the de-sorption of the main products of the catalytic vapor-phase oxidation of propylene, i.e., acrolein and acrylic acid. The presence of the steam with recycle gases such as carbon dioxide also increases the rate of oxygenation.

The first stage of the reaction is performed preferably in the range of 250° C. to 450° C., more preferably 270° C. to 390° C., at a contact time between the reaction mixture and the catalyst preferably from about 0.01 second to 100 seconds, more preferably from 0.1 second to 10 seconds; and a space hourly velocity preferably from about 50 to about 50,000 $h^{-1}$, more preferably from about 100 to 10,000 $h^{-1}$. Reaction product shows a conversion of olefins in the range of preferably not less than 90 mol %, more preferably not less than 97 mol %. In preferred conditions for the second-stage oxidation, the reaction temperature is preferably in the range of 180° C. to 370° C., more preferably 200° C. to 350° C., and the contact time is preferably in the range of 1.0 to 10 seconds, more preferably 1 to 6.0 seconds. The two-stage operation shows a per pass reaction product yield of preferably not less than 85 mol %, more preferably not less than 88 mol %.

The terms "conversion," and "per pass yield," as used herein are defined as follows:

$$\text{Conversion (\%) of olefin} = \frac{\text{Mols of olefin converted}}{\text{Mols of olefin supplied}} \times 100$$

$$\text{Per pass yield (\%) of carboxylic acid} = \frac{\text{Mols of carboxylic acid produced}}{\text{Mols of olefin supplied}} \times 100$$

FIG. 1 is a schematic representation of the two-stage process for the production of carboxylic acid according to an embodiment of the invention. As non-limiting examples, POR can represent a Propylene Oxidation Reactor, AOR can represent an Acrolein Oxidation Reactor, ACE can represent Acrolein, ACA can represent Acrylic Acid. A feed comprising olefin 1 (e.g., propylene) (also steam and inert diluent, e.g., $N_2$, $CO_2$) and oxygen 2 is fed into oxidation reactor 3 (POR) which contains a first stage catalyst 4 (CAT-A) that converts olefin-containing (e.g., propylene) feedstock with oxygen into aldehyde, (e.g., acrolein), water and carbon dioxide. The effluent 5 of POR reactor 1 comprising aldehyde (e.g., ACA), (also unoxidized olefin, e.g., $C_3H_6$; $CO_2$, $N_2$ and $H_2O$), is fed via optional heat exchanger 8 to second stage (AOR) reactor 6 containing catalyst 7 (CAT-B). Heat exchanger 8 allows adjustment of the temperature of the feed to second stage reactor 6. Optionally, the two catalysts CAT-A and CAT-B can be in one reactor in the form of a physical mixture or in alternating layer form (not shown). An appropriate amount of oxygen in line 9 is added to second stage reactor 6, depending upon the process conditions, for the oxidation of aldehyde to carboxylic acid (e.g., acrolein to acrylic acid). Also, by using an appropriate reactor configuration, oxygen can be added via a multi injection system reactor, e.g., where one of the reactants (oxidant) is introduced and controlled through microporous or mesoporous materials or through a configuration of holes placed at regular or random intervals in the reactor (not shown). The effluent 10 from the second stage (AOR) reactor 6 comprising carboxylic acid (e.g., acrylic acid (ACC), also $H_2O$ and $CO_2$), is fed to gas/liquid separation unit 11, where gases including $CO_2$ and nitrogen (inert) are separated from liquid carboxylic acid and water. The inert gas streams 12 comprising $CO_2$ and $N_2$ from gas/liquid separation unit 11 are cycled through carbon dioxide removal unit 13 and the stream 14 from the carbon dioxide removal unit 13 is recycled through lines 20 and 22 to the feedstream 1 to the first stage reactor 3. Optionally, the gas streams 12 can also be recycled to first stage reactor 3 without the carbon dioxide absorption (not shown), as the catalyst 4 (CAT-A) in reactor 3 is not affected by the presence of carbon dioxide. Co-feed of carbon dioxide can also help in controlling the extent of exothermic heat of the reaction. Liquid stream 15 from separator unit 11 is fed to distillation unit 16 where carboxylic acid (e.g., acrylic acid) 17 is separated from water 18, and water 18 can be recycled back to first stage reactor unit 3 via lines 19, 20 and 22. Gases and water in streams 14 and 19 can be combined into stream 20 and partially purged in purge unit 21 to control the build-up of gases before being conveyed to first stage reactor unit 3.

The following examples illustrate the invention, but the invention is not limited to these working examples.

EXAMPLE
First Stage Catalyst (Cat A) Preparation

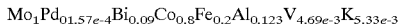
$Mo_1Pd_{01.57e-4}Bi_{0.09}Co_{0.8}Fe_{0.2}Al_{0.123}V_{4.69e-3}K_{5.33e-3}$ Ammonium metavanadate (Aldrich Chemicals, Assay=99.0%) in the amount of 0.11 grams was added in distilled water and heated to 90° C. with stirring. A yellow color solution with pH between 4 and 7 was obtained (Solution A). 8.75 grams of bismuth nitrate, 16.2 grams of ferric nitrate and 46.68 grams of cobaltous nitrate were added with water to solution A with continuous stirring, followed by slow addition of the required amount of palladium, potassium and aluminum salts solution to the mixture. Ammonium paramolybdate tetra hydrated (Aldrich Chemicals A.C.S-12054-85-2) in the amount of 35.4 grams was added to the solution and the mixture was then dried. The resulting solid was dried in an oven at 100° C.–120° C. The dried material was cooled to room temperature and calcined in range of 300° C. to 600° C.

Second Stage Catalyst (Cat B) Preparation

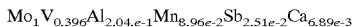
$Mo_1V_{0.396}Al_{2.04.e-1}Mn_{8.96e-2}Sb_{2.51e-2}Ca_{6.89e-3}$

Ammonium metavanadate (Aldrich Chemicals, Assay=99.0%) in the amount of 5.7 grams was added in distilled water and heated to 90° C. with stirring. A yellow color solution with pH between 4 and 7 was obtained (Solution A). 0.45 grams of antimony trioxide and 11 grams of oxalic acid were added with water to the solution with continuous stirring followed by slow addition to the mixture of the required amount of calcium, aluminum, and manganese salts solution. Ammonium paramolybdate tetra hydrated (Aldrich Chemicals A.C.S-12054-85-2) in the amount of 21.7 grams was added to the solution. The resulting solid was dried in an oven at 100° C.–120° C. The dried material was cooled to room temperature and calcined in range of 300° C. to 600° C.

4 cc of 40–60 mesh size of catalyst A was packed into stainless steel tubular reactor (first (I) stage). The reactor was placed in a bubbling sand bath and was heated to 330° C. 4 cc of 40–60 mesh size catalyst B was packed in another tubular reactor (second (II) stage), placed in a similar-type sand bath, and heated to 235° C. The two reactors were interconnected in such a manner that the first stage reactor outlet was introduced into the second reactor containing the second-stage catalyst. A mixed gas containing propylene, oxygen, steam and nitrogen was introduced with a flow of 8 liters/hour to the first (I) stage reactor. An additional amount of oxygen gas was introduced at an intermediate stage between reactor I and reactor II. Outlet gas of the second (II) stage reactor was conveyed to a condenser where acrylic acid was collected in the form of aqueous solution using water containing polymerization inhibitor, hydroquinone. The product showed almost complete conversion of propylene with a 90% yield to acrylic acid. Overall±4 ΔT of the reaction was observed. Reaction was continued over a period of 8000 hours without any sign of deactivation of catalysts.

What is claimed is:

1. A process for production of carboxylic acid using a two-stage catalytic vapor-phase oxidation of olefins comprises introducing into a first stage reactor, a feedstream comprising olefins, oxygen, steam and inert gas;

contacting the feedstream in the first stage reactor with a catalyst composition comprising a catalyst having the formula $$Mo_a Pd_b Bi_c Fe_d X^1_e X^2_f X^3_g O_z$$

wherein $X^1$ = at least one or more of Co, Ni, V, Pt, Rh $X^2$ = at least one or more of Al, Ga, Ge, Mn, Nb, Zn, Ag, P, Si, W $X^3$ = at least one or more of K, Mg, Rb, Ca, Sr, Ba, Na O = oxygen a is 1, $0 < b \leq 0.3$, $0 < c \leq 0.9$, $0 < d \leq 0.9$, $0 < e \leq 0.9$, $0 < f \leq 0.9$, $0 < g \leq 0.3$, z is a number which satisfies the valences of the other elements in the formula, said contacting in the first stage reactor being under reaction conditions sufficient to produce a first stage product comprising aldehyde;

introducing the first stage product into a second stage reactor;

contacting the first stage product in the second stage reactor with a catalyst composition comprising a catalyst having the formula $$Mo_{a_1} V_{b_1} Al_{c_1} X_{d_1} Y_{e_1} O_{z_1}$$

wherein

X = W or Mn or both

Y = at least one or more of Pd, Sb, Ca, P, Ga, Ge, Si, Mg, Nb, K

O is the valence oxygen, and a is 1, b is 0.01 to 0.9, $0 < c \leq 0.2$, $0 < d \leq 0.5$, $0 < e \leq 0.5$, z is a number which satisfies the valences of the other elements in the formula; and said contacting in the second stage reactor being under conditions sufficient to produce a second stage product comprising carboxylic acid.

2. The process of claim 1 further comprising introducing oxygen into the product stream intermediate between the first and second stages or at multistages.

3. The process according to claim 1, wherein the olefins are propylene or isobutylene and carboxylic acids are acrylic acid or methacrylic acid.

4. The process according to claim 1, wherein the feedstream comprises olefins in an amount of about 2% to about 50% by volume, oxygen in an amount of about 3% to about 40% by volume, steam in an amount of about 3% to about 50% by volume, and inert gas in an amount of about 3% to about 80% by volume.

5. The process according to claim 4 wherein the feedstream comprises olefins in an amount of about 5% to about 30% by volume, oxygen in an amount of about 5% to about 30% by volume, steam in an amount of about 5% to about 40% by volume, and inert gas in an amount of about 5% to about 75% by volume.

6. The process according to claim 4 wherein the inert gas comprises nitrogen, propane, argon, carbon dioxide or mixtures thereof.

7. The process according to claim 1, wherein the conditions in the first stage comprise a temperature in the range of about 250° C. to about 450° C. and a pressure of 1 atm to 30 atm, and the conditions in the second stage comprise a temperature in the range of about 180° C. to about 350° C. and a pressure of 1 atm to 30 atm.

8. The process according to claim 1, wherein the oxygen is in the form of molecular oxygen, air or mixture thereof.

9. The process according to claim 1, wherein part of the amount of oxygen is introduced between the first and second stages or at multistages.

10. The process according to claim 9 wherein the part of the amount of oxygen is about 2% to 15% by volume.

11. The process according to claim 1, wherein conversion of olefins in the first-stage reaction is at least 90% and conversion of aldehydes in second-stage reaction is at least 95%.

12. The process according to claim 1, wherein the olefin comprises propylene, the carboxylic acid product comprises acrylic acid, and conversion of propylene in a once through process produces at least 88% acrylic acid product yield.

13. The process according to claim 1, wherein oxygen is supplied as a molecular oxygen-containing gas having purity of at least 90% by volume.

14. The process according to claim 1, wherein the olefins comprise ethylene, propylene, iso-butylene, or n-butylene; the aldehydes comprise acetaldehyde, acrolein or methacrolein; and carboxylic acids corresponding to the aldehydes are produced in the process.

15. The process according to claim 1, wherein the second stage product further comprises off-gas, and the process further comprises separating the off-gas from the carboxylic acid product of the second stage, and recycling the off-gas to the first-stage.

16. The process according to claim 15, wherein the separated off-gas contains steam which is recycled to the first stage.

* * * * *

UNITED STATES PATENT AND TRADEMARK OFFICE
CERTIFICATE OF CORRECTION

PATENT NO. : 6,441,227 B1
DATED : August 27, 2002
INVENTOR(S) : Karim et al.

It is certified that error appears in the above-identified patent and that said Letters Patent is hereby corrected as shown below:

Column 4,
Line 22, please replace "$0<g<0.3$" with -- $0<g\leq 0.3$ --

Signed and Sealed this

Thirty-first Day of December, 2002

JAMES E. ROGAN
*Director of the United States Patent and Trademark Office*